US005763455A

United States Patent [19]

Davies et al.

[11] Patent Number: 5,763,455
[45] Date of Patent: *Jun. 9, 1998

[54] BIOLOGICALLY ACTIVE TROPANE DERIVATIVES

[75] Inventors: Huw M. L. Davies, Williamsville, N.Y.; Steven R. Childers, Winston-Salem, N.C.

[73] Assignee: Wake Forest University, Winston-Salem, N.C.

[ * ] Notice: The term of this patent shall not extend beyond the expiration date of Pat. No. 5,760,055.

[21] Appl. No.: 874,940

[22] Filed: Jun. 13, 1997

Related U.S. Application Data

[60] Division of Ser. No. 589,820, Jan. 22, 1996, which is a continuation-in-part of Ser. No. 63,431, May 18, 1993, which is a continuation-in-part of Ser. No. 851,090, Mar. 13, 1992, Pat. No. 5,262,428.

[51] Int. Cl.$^6$ ............................. A01N 43/42; A61K 31/44
[52] U.S. Cl. ................................ 514/304; 546/124
[58] Field of Search ............................ 514/304; 546/124

[56] References Cited

U.S. PATENT DOCUMENTS

| 3,120,537 | 2/1964 | Archer et al. | 546/124 |
| 3,813,404 | 5/1974 | Clarke et al. | 546/124 |
| 5,128,118 | 7/1992 | Carroll et al. | 424/1.1 |
| 5,374,636 | 12/1994 | Moldt et al. | 514/304 |

OTHER PUBLICATIONS

Madras et al., Molecular Pharmacology, 35:518–524, 1989.
Davies et al., Tetrahedron Letters, vol. 30, No. 35, pp. 4653–4656, 1989.
Boja et al., European Journal of Pharmacology, 184, pp. 329–332, 1990.
Carroll et al., Journal of Medicinal Chemistry, vol. 34, No. 9, pp. 2719–2725, 1991.
Clarke et al., Journal of Medicinal Chemistry, vol. 16, No. 11, pp. 1260–1267, 1973.
Davies et al., American Chemistry Society, Dec. 5–7, pp. 181–182, 1990.
Lewin et al., Journal of Medicinal Chemistry, vol. 35, No. 1, 1992, pp. 135–140.
Abraham et al., Journal of Medicinal Chemistry, vol. 35, No. 1 1992, pp. 141–144.
Kozikowski et al., Medicinal Chemistry Research, vol. 1, pp. 312–321, 1991.
Davies et al., J. Organic Chemistry, vol. 56, 19, 1991, pp. 5695–5700.
Porinno, L.J. et al., J. Pharmacol. Exp. Ther. 1995, vol. 272, pp. 901–910.
Hemby, S.E. et al., The Journal of Pharmacology and Experimental Therapeutics, vol. 273, No. 2 (1995) pp. 656–666.

*Primary Examiner*—Kimberly Jordan
*Assistant Examiner*—Dwayne C. Jones
*Attorney, Agent, or Firm*—Zarley, McKee, Thomte, Voorhees, & Sease

[57] ABSTRACT

Selective blockade of DA and 5-HT uptake sites with 3-aryltropane derivatives.

11 Claims, No Drawings

BIOLOGICALLY ACTIVE TROPANE DERIVATIVES

CROSS-REFERENCE TO A RELATED APPLICATION

This application is a divisional of Ser. No. 08/589,820 filed Jan. 22, 1996, which was a continuation-in-part of Ser. No. 08/063,431 filed May 18, 1993, which was a continuation-in-part of Ser. No. 07/851,090 filed Mar. 13, 1992, now U.S. Pat. No. 5,262,428 issued Nov. 16, 1993.

GRANT REFERENCE CLAUSE

This invention was made with government support under R01-DA-6301-02 and P50-DA06634 awarded by the National Institute on Drug Abuse. The government has certain rights in this invention.

BACKGROUND OF THE INVENTION

The tropane skeleton is a basic structural unit that can lead to compounds with diverse central nervous system activity. Due to the rigid nature of the structure, the possibility exists for the preparation of highly selective compounds. This application describes the synthesis of tropane derivatives that selectively bind to monoamine neurotransmitters and thus have the potential for the treatment of major depression, attention-deficit hyperactivity disorder, obesity, obsessive compulsive disorders, and cocaine addiction.

Major depression represents one of the most common mental illness, affecting between 5–10% of the population. The disease is characterized by extreme changes in mood which may also be associated with psychoses. The etiology of depression has been linked to deficiencies in one or several of the monoamine neurotransmitters, including serotonin, norepinephrine, and dopamine. Thus, drug treatment is generally directed towards replenishing these neurotransmitters in the brain and different antidepressants are directed towards the replenishment of particular neurotransmitters depending on the patient's deficiency.

For over thirty years, the tricyclic antidepressants, such as imipramine, have been classically used for the treatment of depression. Their mechanism of action consists of blocking the monoamine reuptake pump, thus permitting the neurotransmitter to be in contact with the receptor site for a longer period of time. Their ability to inhibit the neuronal uptake of norepinephrine is believed to be a major factor behind their efficacy. However, their use is limited by development of significant adverse side effects.

To address these concerns, a number of new types of antidepressants have been developed in recent years. Two compounds marketed in the U.S. are trazodone and fluoxetine (Prozac®). Both of these compounds interact with the regulation of serotonin (5-HT). Trazodone controls the actions of 5-HT while fluoxetine is a potent and selective inhibitor of 5-HT reuptake. 3-Chloroimipramine which inhibits both 5-HT and norepinephrine reuptake has been extensively used as an antidepressant in Europe and Canada. Other compounds which are of current interest or have been examined as antidepressants include fluvoxamine, citalopram, zimeldine, sertraline, bupropion and nomifensine. All of these drugs inhibit monoamine uptake mechanisms, but differ in selectivity between the dopamine, 5-HT and norepinephrine transporters.

Considerable attention has recently been directed to the condition known as attention-deficit hyperactivity disorder (ADD). Children with this condition tend to be very active physically but have great difficulty with situations requiring long periods of attention. Consequently, they tend to underachieve academically and can be very disruptive. Furthermore, these behavioral problems often persist in modified forms into adulthood. The condition appears to be associated to the effect of monoamines in the cerebral cortex, which are involved with control of attention. A number of stimulant drugs such as dextroamphetamine, methylphenidate as well as the tricyclic antidepressants, antipsychotic agents and clonidine have been used as medications to control the disorder. Many of these drugs interact with the monoamine uptake transporters.

Recently, serotonin uptake inhibitors, such as fluoxetine, have been prescribed for the treatment of obesity. Anorexia and weight loss are side effects commonly associated with serotonin uptake inhibitors. Further, serotonin uptake inhibitors have been used in the treatment of obsessive-compulsive disorders, such as bulimia, which have also been associated with monoamine neurotransmitter deficiencies.

Cocaine addiction represents a major societal problem. The development of compounds that can modify the biological actions of cocaine would be very beneficial for the treatment of cocaine addiction. Cocaine is an inhibitor of both the dopamine and serotonin transporters, and so potent and selective compounds for these transporters can modify the biological consequences of cocaine.

It has previously been shown that cocaine and related compounds are potent inhibitors of dopamine reuptake and this leads to compounds with reinforcing properties. In recent years a number of new extremely potent cocaine analogs have been, prepared based on the tropane structure. These compounds tend to selectively bind to the dopamine transporter and certain structural variations of the tropane skeleton can lead to compounds that bind with very high selectivity to the dopamine reuptake site. (Carroll et al. Journal of Medicinal Chemistry, 1992, 35, 2497). Only a few tropane derivatives have been prepared that exhibit a higher affinity for binding to the 5-HT transporter compared to the dopamine transporter (Boja, J. W. et al. *J Med. Chem.* 1994, 31, 1220). All of these tropane derivatives are very similar to each other because they are all derived from cocaine as a starting material.

In principle, the tropane skeleton is ideally suited to prepare highly selective compounds because it is a rigid structure and so derivatives will have rather limited conformational flexibility. It would therefore be very valuable if the binding selectivity of the tropane skeleton could be altered by appropriate structural changes so that analogs favoring binding to the 5-HT reuptake site could be prepared. The previous related patent applications disclosed how the novel chemistry that has been developed enabled the preparation of a much wider range of tropane analogs than was previously accessible, leading to novel structures with moderate potency and improved selectivity for the 5-HT transporter (Davies H. M. L. et al. *Eur. J. Pharmacol* 1993, 244A, 93–97; Davies, H. M. L. et al. *J. Med. Chem.* 1994, 37, 1262–1268; Benrett, B. A. et al. *Pharmacol. Exp. Ther.* 1995, 272, 1176–?).

It has now been discovered that if the tropane system is modified, particularly at the aryl moiety as hereinafter described, compounds can be produced that are up to 400 times more potent at the 5-HT transporter and up to 10 times more selective for the 5-HT transporter than those that were described in application Ser. No. 063,431. Since these tropanes (as described below) bind selectively to the 5-HT transporter, they also selectively inhibit 5-HT transport, thus increasing synaptic levels of 5-HT. This discovery will be helpful in treating diseases related to 5-ET function.

According, it is a primary objective of the present invention to provide a process for the development of tropane analogs which bind more selectively to the 5-ET transporter than compounds previously described.

Another primary objective of the present invention is to prepare a range of tropane analogs which can be investigated as drugs for the treatment of chronic depression.

Another primary objective of the present invention is to prepare a range of tropane analogs which can be investigated as drugs for the treatment of cocaine addictions Another objective of the present invention is to prepare a range of tropane analogs which can be investigated as drugs for the treatment of obesity, attention-deficit disorder, and obsessive-compulsive disorder.

A still further objective of the present invention is to prepare a wide range of tropane derivatives which can be systematically used and tested to determine structure-activity relationships for binding at dopamine, 5-HT and norepinephrine transporters.

SUMMARY OF THE INVENTION

Biologically active derivatives of the tropane ring system are provided which selectively bind either to the serotonin (5-HT) or dopamine (DA) reuptake site, leading to compounds which have use for the treatment of clinical depression, ADD, obesity, obsessive-compulsive disorder, and cocaine addiction.

3-aryltropane derivatives are prepared by reacting 8-azabicyclo[3.2.1] oct-2-ene with an aryl Grignard reagent in the presence of catalytically effective amounts of copper (I) and/or copper (II) salts. The 3-aryl-tropane derivative starting material can be conveniently prepared by decomposing functionalized vinyldiazomethanes in the presence of certain pyrroles preferably in substantial excess of the stoichiometric amount, using a decomposition catalyst, preferably a rhodium catalyst. The catalyst may also be a copper, palladium or silver salt catalyst. This provides a bicyclic intermediate containing the basic tropane ring system which is thereafter converted to an 8-azabicyclo [3.2.1] oct-2-ene, which itself may be used as a starting material to react with aryl Grignard reagent in providing the synthesis route to the unique tropane analogs of the present invention.

DETAILED DESCRIPTION OF THE INVENTION

The focus of this application will be on novel tropane derivatives and their salts having the general formula (1):

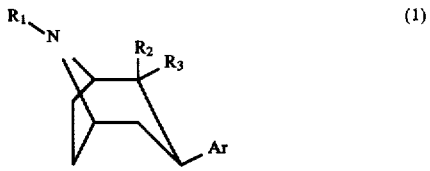

(1)

Wherein Ar is an aromatic moiety selected from the group consisting of 1-naphthyl, 2-naphthyl, 4-(substituted C1 to C8 alkyl)-1-naphthyl, 6-(substituted $C_1$ to $C_8$ alkyl)-2-naphthyl, 6-methoxy-5-substituted-2-naphthyl (where the 5-substituent is $C_1$ to $C_8$ alkyl, iodo, nitro or acyl), phenyl, 4-(substituted $C_1$ to $C_8$ alkyl)phenyl, 4-substituted vinylphenyl, and 4-(substituted $C_1$ to $C_8$ 1-alkenyl) phenyl moiety, and providing that when $R_1$ is methyl and Ar is a naphthyl group that Ar is substituted at the 5 position and further providing that when Ar is 1-naphthyl or 2-naphthyl that $R_1$ is hydrogen. Preferred are vinylphenyl; and 4-(substituted $C_1$ to $C_8$ 1-alkenyl) phenyl moiety. $R_1$ may be hydrogen, or $C_1$ to $C_8$ alkyl. $R_2$ and $R_3$ may be the same or different and are selected from the group consisting of hydrogen and $C_1$ to $C_8$ ketones with only one of $R_2$ and $R_3$ being hydrogen at any one time.

The preferred compounds for use in the present invention are of formula 2:

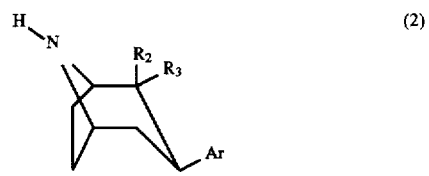

(2)

Wherein Ar, $R_2$, and $R_3$ are the same as described above.

The very most preferred compounds for use in the present process are of formula 3:

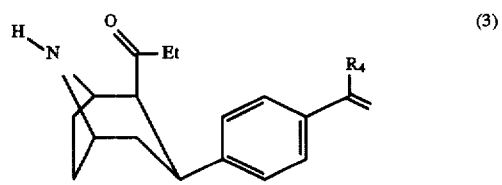

(3)

Wherein $R_4$ may be hydrogen, or $C_1$ to $C_8$ alkyl and Et is ethyl.

One of the present inventors, namely Dr. Huw M. L. Davies, has previously published concerning the general synthesis used for the starting material of the parent case, namely synthesizing 8-azabicyclo [3.2.1]oct-2-ene of the above formula. In this regard see, Davies,, et al., "Novel Entry to the Tropane System by Reaction of Rhodium (II) Acetate Stabilized Vinylcarbenoides with Pyrroles," *Tetrahedron Letters*, vol. 30, no.35, pp. 4653–4656, (1989) a December 1990 abstract of a regional ACS meeting held in New Orleans, entitled Davies, et al., "Chemistry of Vinylcarbenoids with a Single Electron Withdrawing Group, an Approach to Tropane Alkaloids", American Chemical Society, Dec. 5–7, 1990, pp. 181–182; Davies, et al., "Synthesis of±Ferruginine and Anhydroecgonine Methyl Ester by a Tandem Cyclopropanation/Cope Rearrangement", *Journal of Organic Chemistry*, 1991, Vol. 56, pp. 5696–5700. The subject matter of each of these publications of Davies et al. is incorporated herein by reference and therefore need not be described in full detail. However, certain preferred process operations, not specifically mentioned in the above articles, are described herein for the sake of completeness.

Preparation of the starting material for the Grignard addition of the present invention, namely, preparation of 8-azabicyclo[3.2.1]oct-2-ene as above described employs in its first step a process of decomposing of a functionalized vinyldiazomethane of the formula:

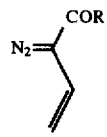

in the presence of at least a stoichiometric amount of a pyrrole of the formula:

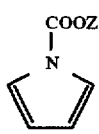

wherein Z is a functional group protector, and also in the presence of a small but effective amount of a decomposition catalyst selected from the group consisting of rhodium, copper, palladium and silver salts, to provide an intermediate bicyclic compound.

R as shown above represents a $C_1$ to $C_8$ so that the resulting analog of cocaine ultimately prepared will have a ketone group at the two position. In the pyrrole, Z represents a functional group protector such as trimethylsilylethyl, although it is understood that other classic protecting groups such as tertiarybutyl group may also be employed.

The amount of the pyrrole for this first reaction scheme needs to be at least a stochiometric amount in comparison with the vinyldiazomethane and preferably is in excess of the stoichiometric amount, perhaps within the range of a two-fold to a five-fold excess. An excess is preferred in terms of achieving the desired high yields of the bicyclic intermediate because the vinyldiazomethane is decomposed to a very reactive intermediate, namely a vinylcarbenoid which will, unless it is trapped by use of stoichiometric excesses of the pyrrole, rapidly decompose.

The pyrroles above described can be conventionally prepared using well known chemistry as described in the *Journal of Organic Chemistry*, 1991, vol. 56 article, of the author earlier cited. The reaction is preferably run at temperature of within the range of from 25° C. to about 100° C., preferably at about 80° C. The reaction can be run at 25° C. if there is slow addition of the vinyldiazomethane to the pyrrole. The pressure is not critical in this reaction step.

As explained above, the reaction is conducted in the presence of a decomposition catalyst selected from the group consisting of rhodium, copper, palladium and silver salts. Preferably the catalyst is a rhodium salt catalyst and may be a rhodium (II) acetate, mandelate, trifluoroacetate, hexanoate, pivalate or octanoate. The presently most preferred catalyst is rhodium octanoate which seems to allow higher yields of desired product. The amount of catalyst may vary from 0.1 mole per cent to about 10 mole per cent of the vinyldiazomethane, and is preferably about 1.0 mole per cent of the amount of the vinyldiazomethane reactant.

Reaction time does not appear to be critical and the time may vary from a few minutes up to several hours if drop wise addition is accomplished. The other carbon atoms of the 8-azabicyclo[3.2.1]oct-2-ene can include substituents other than hydrogen (e.g. one or more of the other carbon atoms of the bicyclic system can include a lower alkyl substituent group) because a more highly substituted pyrrole or vinyldiazomethane may be used as starting material.

The first step reaction produces an intermediate bicyclic compound which upon hydrogenating, removal of the deprotective group and reductive methylation is converted to the earlier described 8-azabicyclo[3.2.1]oct-2-ene. The hydrogenation, deprotecting and reductive methylation are all well known steps and need not be described herein.

Where R equals methyl and the protecting group used is trimethylsilyl the intermediate is methyl 8-(2-(trimethylsilyl)ethoxycarbonyl)-8-azabicyclo [3.2.1]octa-2, 6-dien-2-oate.

This reaction is preferably conducted in the presence of a solvent and the solvent is preferably a non-polar solvent. Suitable non-polar solvents for conducting this reaction may be pentane, hexane, and benzene. Other suitable non-polar solvents, capable of dissolving the basic reactants may also be employed, with the precise solvent not being critical, as long as it is in fact non-polar.

For details of the hydrogenating, deprotecting and reductive methylation see, the previously incorporated by reference 1991 vol. 56, *Journal of Organic Chemistry* article. There it is basically described that the catalytic hydrogenation is a process employing a Wilkinson's catalyst and that deprotection occurs with, for example, tertiarybutyl ammonium fluoride to give the desired 8-azabicyclo [3.2.1]oct-2-ene at yields as high as 95%. As explained in the earlier referenced article, the composition is purified by silica gel column chromatography.

The 8-azabicyclo[3.2.1]oct-2-ene is then used as a starting material for the process of the present invention. It has been found that the 8-azabicyclo [3.2.1]oct-2-ene formula earlier described, can be converted to biologically active cocaine analogs having a wide variety of active analog structures by reacting with a an aryl Grignard reagent in the presence of a catalytically effective amount of a copper salt catalyst. The copper salt catalyst may be a copper (I) or copper (II) catalyst.

As previously described, it is preferred that the R group of the 8-azabicyclo[3.2.1]oct-2-ene be C1 to C8 alkyl, rather than an oxyalkyl since it is preferred that the two substituent be a ketone substitution rather than an ester substitution. The ketones behave better in the copper catalyzed reaction, and as explained later in the biological activity section of the specification, should have higher metabolic stability and have equivalent binding site activity. The Grignard addition reaction is run in a suitable non-polar organic solvent, preferably ether or tetrahydrofuran.

The Grignard reagent (ArMgX) may be any suitable aryl magnesium halide. The aryl group may be 1-naphthyl, 2-naphthyl, 4-(substituted $C_1$ to $C_8$ alkyl)-1-naphthyl, 6-(substituted $C_1$ to $C_8$ alkyl)-2-naphthyl, 6-methoxy-5-substituted -2-naphthyl (where the 5-substituent is $C_1$ to $C_8$ alkyl, iodo, nitro or acyl), phenyl, 4-(substituted $C_1$ to $C_8$ alkyl)phenyl, 4-substituted vinylphenyl, and a 4-(substituted $C_1$ to $C_8$ 1-alkenyl)phenyl moiety. The "X" moiety represents a halide group and is preferably bromide. The copper salt may be a copper (I) or (II) salt and can be, for example, copper bromide dimethyl sulfides The amount of the Grignard reagent is preferably an excess of the stoichiometric amount in order to assure completion of the reaction. Suitable high yields are obtained when an excess of up to four-fold of the Grignard reagent is employed. As set forth below, in order to achieve synthesis of compounds without an alkyl group on the nitrogen atom, an excess of Grignard reagent must be employed so that there is leftover reagent to react at the aryl position. The amount of the copper salt catalyst can be from 5% (molar) to 20% (molar) of the Grignard reagent, and is preferably 15 mole percent of the amount of the Grignard reagent.

The reaction product is a mixture of two structural isomers, one with the 2-moiety position upwardly and second with the 2-moiety position downwardly. Those analogs that are most preferred are the analogs wherein R is alkyl and therefore the two position moiety is a ketone moiety, and that the structural isomer is with the ketone groups in an up position. These are far more active in binding assays, than the downward structural isomers and in some instances as much as 200 times more active in site-binding.

Certain other process conditions are worthy of mention. The reaction is not temperature critical and may be run at anything from 0° C. or lower up to room temperature, or even higher. The reaction is preferably run under an inert gas atmosphere. The reaction is substantially immediate and therefore may be run from a few minutes to as much as twelve hours. Preferably the reaction occurs under stirring in order to assure completeness. After completion, the reaction can be quenched with for example HCl in ether at −78° C. followed by treatment with water and warming, with the desired compound extracted with ether. It may be purified as illustrated in the examples by conventional silica gel chromatography.

Prior to this application, it was not realized that the preferred compounds containing the hydrogen group on the nitrogen atom could be synthesized using the above scheme. Normally, the Grignard reagent reacts in an acid/base manner with a hydrogen on the nitrogen atom and would be destroyed. Surprisingly, the inventors discovered that by using an excess of the Grignard reagent, it was possible to achieve an effective addition of the aryl group to the tropane ring without interference from the initial acid/base reaction at the nitrogen-hydrogen bond.

The compounds may be administered orally, parentally, or intravenously. The preferred route of administration is oral. The dose levels may be from 4 micrograms per kilogram of body weight up to 50 milligrams/Kg of body weight and more typically from 20 micrograms/Kg up to 15 mg/Kg.

Other ingredients may be added to the compounds as part of a pharmaceutical composition depending on the type of dosage form, particular needs of the patient, and method of manufacture. Examples include but are not limited to binders, lubricants, fillers, flavorings, preservatives, colorings, diluents, etc. The selection of particular substances and their compatibilities with the compositions of the present invention can be readily ascertained by those of ordinary skill in the art.

The novel tropane analogs synthesized by the vinylcarbenoid scheme listed above were tested for their ability to interact with 5-HT and dopamine transporters by displacement of radioligand binding to transporter sites. Low concentrations (10–20 pM) of $[^{125}I]$RTI-55, the potent tropane analog recently synthesized by Carroll's group (Boha et al., *European Journal of Pharmacology*, 1991, 184, 329), was used to label dopamine transporters in rat striatal membranes, while [3H]paroxetine (Habert et al., *European Journal of Pharmacology*, 1985, 118, 107) was used to label 5-HT transporter sites in rats frontal cortex and [3H] nisoxetine was used to label the NE transporter sites. Up to the present time, 22 new analogs have been tested for binding; their potencies in binding assays are summarized in Table 1.

In the previous continuation-in-part, the synthesis and utility of a series of novel tropanes was described. The synthesis of these compounds was based on a new synthetic method to the tropane. Entries 1–4 in Table 1 are used to illustrate the most significant binding results that were described in the previous patent.

In Table 1, the general formula is that depicted in the earlier part of this application, just at the beginning of the heading "Detailed Description of the Invention". Code names, as presented, WF-1 through WF-60, are internal names of the assignee and simply stand for "Wake Forest-1" etc.

Entries 11–26 represent compositions of the current invention while Entries 1–10 are compositions from the previous continuations-in-part. The general formula as depicted in the current application is also applicable to the previously disclosed compositions. For each composition in Table 1, $R_2$ represents ethyl ketone and $R_3$ is hydrogen.

These specific groups were tested for purposes of convenience and consistency, but it should be appreciated that $R_2$ and $R_3$ may be interchanged, as demonstrated in Table 1 of Ser. No. 063,431 wherein several of the compositions tested had a ketone at the $R_3$ position and hydrogen at the $R_2$ position. Furthermore, it can be predicted that the other lower alkyl ($C_1$ to $C_8$) ketones will behave comparatively to ethyl ketone in so far as their binding affinities to dopamine, serotonin and norepinephrine transporters.

The binding affinity of tropane derivatives at the dopamine transporter was the basis of the original patent on drugs for the treatment of cocaine addiction. In the original application, the binding affinities for WF 1–5, 7–9, and 11 were reported as background evidence. Since then, a publication with the binding affinities for WF 1–5, 7–9, 11, 13, 18, 19, 22, 23, 25 has appeared (Davies, et al., *European Journal of Pharmacology— Molecular Pharmacology Section*, 1993, 244,93).

In the previous continuation-in-part (Ser. No. 08/063, 431), PTT (WF-11), PIT (WF-31), WF-23, and WF-33 were tested for their ability to displace cocaine from $[^{125}I]$RTI-55 binding which measured their ability to bind to the dopamine transporter as well as their ability to bind to the 5-HT transporter. The application demonstrated that the 2-naphthyl analogs, WF-23 and WF-33 were the most potent compounds in regard to their their affinity for binding to DA and 5-HT transporters.

In the present application, the inventors have synthesized novel tropane derivatives which are up to 10 times more selective for the 5-HT transporter than those described in Ser. No. 063,431 which are also up to 400 times more potent at the 5-UT transporter. Since these tropanes bind preferentially to the 5-HT transporter, they also preferentially block 5-HT transport, thus increasing synaptic levels of 5-HT. This discovery will lead to the improved treatment of diseases related to inadequate serotonin function.

The p-tolyl derivative (WF11, for references on recent in vivo biological studies on this compound, see Porrino, L. J. et al. *Life Sciences*, 1994, 54, 511.47 (b) Hemby, S. E. et al. *J. Pharmacol. Exp. Ther.* 1995, 272, 1176–1186 (c) Porrino, L. J. et al. *J. Pharmacol Exp. Ther.*1995, 272, 901) and the 1-naphthyl derivative (WF30) represent prototypical members of the class of tropanes that can be derived from this chemistry. Many compounds with binding affinity in the 1–20 nM were prepared and in general these compounds were moderately selective for the dopamine transporter.

In contrast, the 2-naphthyl derivative (WF23) was the most potent tropane analog that has been prepared, although it was unselective since it displayed approximately equal affinities at both dopamine and serotonin transporters. However, introduction of bulky aryl substituents as seen with the 4-isopropyl phenyl derivative (WF31) resulted in a compound that was relatively selective for the 5-HT transporter. The 5-HT selectivity seen with (WF31) is in sharp contrast to that of most of the previously prepared tropane analogs as these tended to be more potent in binding to the dopamine transporter.

Another approach that leads to enhanced 5-HT selectivity has been to prepare N-demethylated tropane derivatives, although this approach had previously not yet resulted in tropanes that display high selectivity for the 5-HT transporter. In this present application, the structure is disclosed of novel tropanes that have structural elements such that the increased potency seen with naphthyl derivatives is combined with structural elements that increase serotonin selectivity as seen in bulky aryls substituted and N-demethylated derivatives. This led to compounds with very high affinity and selectivity at the 5-HT transporter. Most notably the 4-(1-methylethenyl)phenyl derivative (WF60) is over 300 times more potent and over 15 times more selective than the previous most 5-HT-selective compound (WF31) described in the previous continuation-in-part (Ser. No. 063,431).

Table 1 demonstrates the binding affinities of a series of tropanes to the dopamine (DA), serotonin (5-HT) and norepinephrine (NE) transporters. The first series of derivatives are 4-substituted 1-naphthyl derivatives (entries 5–7). On increasing the size of the 4-substituent from hydrogen to methyl, a four fold decrease in DA potency and a 3-fold increase in 5-HT potency was observed, such that the 4-methylnaphthyl derivative (WF27) is now moderately 5-HT selective. On increasing the size of the alkyl group further, improved selectivity towards 5-HT over NE is observed, but the selectivity towards DA is not further enhanced because there is a gradual erosion of binding affinity towards both the DA and the 5-HT transporters.

The next series of derivatives were the 6-substituted 2-naphthyl derivatives (entries 8–10). The 2-naphthyl functionality leads to the most potent tropanes known to date, and introduction of a 6-methyl (WF40), 6-isopropyl (WF41) or a 6-methoxy group (WF33) results in very little change in potency or selectivity. Addition of further bulky substituents at the 5-position, however, did enhances selectivity towards the 5-HT transporter (entries 11–15). All of these derivatives were less potent at the DA transported than the 6-substituted derivatives (entries 8–10) and two derivatives in particular displayed good binding selectivity for the 5-HT transporter. The 5-nitro derivative (WF44) had a Ki value of 15 nM for binding at the 5-HT transporter and a 5-HT/DA binding potency ratio of 10 and 5-HT/NE binding potency ratio of 60 while the 5-ethyl derivative (WF 52) had a Ki value of 7.2 nM for binding at the 5-HT transporter and a 5 HT/DA binding potency ratio of 5 and 5-HT/NE binding potency ratio of 470.

Further enhancement in 5-HT selectivity was seen in N-demethylated derivatives (entries 16–26). The demethylated 2-naphthyl derivative (WF51) retains potency at all the transporters but the tolyl (WF49) and the isopropyl derivatives (WF50) have about a ten fold increase in 5-HT potency. Consequently, the isopropyl derivative (WF50) has 5.3 nM binding affinity at 5-HT site with a 5-HT/DA selectivity of 72 and a 5-HT/NE selectivity of 640. A limit exists for the ideal size of the alkyl group as both the 3-pentyl and the cyclohexyl derivatives (WF61 and WF63), were considerably less potent than the isopropyl derivative (WF31), and the demethylated derivatives (WF62 and WF64) had only a moderate improvement of 5-HT selectivity over (WF61 and WF63).

The final group of compounds has extended unsaturation and bulk on the para substituents. This modification resulted in highly potent and 5-HT selective compounds. The 5-HT binding affinity of the vinyl derivative (WF55) was 3.2 nM while the dopamine binding affinity was 0.95 nM. The demethylated analog (WF58) had a 10 fold increase in potency at 5-HT over WF55 with little change in potency at the DA transporter. This resulted in the first example of a tropane with sub-nanomolar binding to the 5-HT transporter (0.32 nM) and moderate 5-HT/DA selectivity (5). Further improvement of this trend was possible by using the slightly bulkier isopropenyl substituent. Even the N-methylated compound (WF54) displayed sub-nanomolar binding affinity at 5-HT (0.32 nM) and a good 5-HT/DA potency ratio (9). This effect was further enhanced in the N-demethylated derivative (WF60) leading to a compound that has 5-HT binding affinity of 0.01 nM with a 5-HT/DA potency ratio of 160 and a 5-HT/NE ratio of 940. These compounds represent the first examples of tropanes that have sub-nanomolar binding affinity and high selectivity at the 5-HT transporter.

The following example demonstrates the general method for synthesizing the compounds set forth in Table 1. It is for illustrative purposes only and is not meant to limit the present invent4ion in any manner.

EXAMPLE

Ether and THF were distilled from sodium benzophenone ketal under Ar. Petroleum ether refers to that fraction boiling in the range 40°–60° C. Flash chromatography was carried out on a silica gel (Grade 60, 230–400 mesh). $^1H$ and $^{13}C$ NMR spectra were recorded for solutions in $CDCL_3$ at 200 and 50.3 MH, respectively on a Varian VXR200 instrument. Chemical shifts are quoted in ppm relative to TMS. The N-methyl derivatives series were prepared by the general procedure described previously in the continuation-in-part, U.S. Pat. No. 5,262,428. General Procedure for the NH derivatives. The arylmagnesium bromide (10–15 equiv) in ether/THF was added to thoroughly dried copper bromide-dimethyl sulfide complex (1–2 equiv). The mixture was stirred at room temperature for 10–45 minutes and then cooled to 0° C. A solution of 2-propanoyl-8-azabicyclo [3.2.1]oct-2-ene(8, 1 equiv) in dry solvent was added dropwise. The solution was allowed to stir at 0° C. for 4–6 h, then overnight at room temperature. The solution was next cooled to —75° C. and a solution of $HCl_{(g)}$ dissolved in dry ether (pH=2) was added very carefully keeping the temperature below −70° C. at all times. Upon completion of the quench, the reaction mixture was poured on to ice and the mixture was allowed to warm to room temperature. The organic layer was separated and washed thoroughly with aqueous HCl solution (9%). The combined aqueous solutions were basified with aqueous $NH_4OH$, saturated with NaCl and extracted fully with $CH_2Cl_2$. The combined extracts were dried ($Na_2SO_4$), evaporated and subjected to flash chromatography on a silica column (5"×1") using the eluent indicated to give the following tropanes:

8-Methyl-3β-(1-(4-methylnaphthyl))-2β-(propanoyl)-8-azabicyclo [3.2.1]octane (WF-27). (9/1 ether/triethylamine—8.75/0.25/1 ether/methanol/triethylamine) 73% yield: IR (neat)2920, 1700, 1670, 1580, 740, 715 cm$^{-1}$; $^1H$ NMR (CDCl$_3$)δ8.01 (t, 1H, J=2.2 Hz), 7.97 (t, 1H, J=2.4 Hz) 7.53 (d, 1H, J=7.6 Hz), 7.46(d, 1H, J=5.9 Hz), 7.48 (d, 1H, J=7.8 Hz), 7.28 (d, 1H, J=7.8 Hz), 3.75 (dt, 1H, J=12.9, 4.9 Hz), 3.51 (dd, 1H, J=6.7, 2.5 Hz), 3.44 (dd, 1H, J=6.4, 2.6 Hz), 3.17 (t, 1H, J=3.6 Hz), 2.95 (ddd, 1H, J=12.7, 12.7, 2.8 Hz), 2.62 (s, 3H), 2.34 (q, 2H, J=7.3 Hz), 2.25 (s, 3H), 2.01–1.74 (m, 4H), 1.59 (dt, 1H, J=12.4, 3.6 Hz), 0.69 (t, 3H, J=7.3 Hz); $^{13}C$ (CDCl$_3$)δ 209.7, 135.5, 132.8, 132.4, 131.4, 126.6, 126.5, 126.4, 125.3, 124.6, 122.9, 64.6, 62.7, 57.5, 42.1, 35.2, 34.9, 30,6, 27.6, 25.2, 19.4, 7.6; MS m/z (relative intensity) 321(44), 264(100), 207(3), 179(5), 165(6), 97(42), 82(44), 57(4); HRMS calcd for $C_{22}H_{27}NO$ 321.2096, found 321.2092.

3β-(1-(4-Ethylnaphthyl))-8-methyl-2β-(propanoyl)-8-azabicyclo [3.2.1]octane (WF-42). (98/2 ether/triethylamine-85/10/5 ether/triethylamine/methanol),. 6% yield; IR (neat)2936, 2875, 1719, 1691, 1514, 1416, 1374, 1310, 1242, 1204, 1130, 1050, 919, 880, cm$^{-1}$;$^1H$ NMR (CDCl$_3$)δ 8.09–7.97 (m, 2H), 7.58(d, 1H, J=7.6 Hz), 7.47 (m, 2H), 7.31 (d, 1H, J=7.6 Hz), 3.75 (m, 1H), 3.49 (m, 2H), 3.17 (m, 1H), 3.04 (q, 2H, J=7.6 Hz), 2.96 (ddd, 1H, J=13.0, 13.0, 2.4 Hz), 2.40–2.21 (m, 2H), 2.26 (s, 3H), 2.00–1.55 (m, 5H), 1.33 (t, 3H, J=7.5 Hz), 0.70 (t, 3H, J=7.3 Hz); $^{13}C$ (CDCl$_3$)δ 209.7, 138.3, 135.4, 132.0, 131.6, 126.6, 125.2, 124.9, 124.8, 124.6, 123.1, 64.7, 62.8, 57.5, 42.2, 35.2, 35.0, 30.7, 26.7, 25.8, 25.3, 14.9, 7.7; MS m/z (rel intensity) 335 (42), 278 (100), 250 (1), 193 (9), 178 (12), 165 (21), 153 (16); Anal. Calcd. for C$_{23}$H$_{29}$NO·0.5 H$_2$O: C, 80.19; H, 8.78; N, 4.07 Found C, 80.41; H, 8.61; N, 3.93.

3β-(1-(4-Isopropylnaphthyl))-8-methyl-2β-(propanoyl)-8-azabicyclo [3.2.1]octane (WF-38).

(98/2 ether/triethylamine-85/10/5 ether/triethylamine/methanol), 37.7% yield: IR (neat) 2958, 2936, 2874, 1718, 1691, 1514, 1459, 1416, 1351, 1225, 920, 825 cm$^{-1}$; $^1$H NMR (CDCl$_3$)δ 8.15 (m, 1H), 8.01 (m, 1H), 7.62 (d, 1H, J=7.6 Hz), 7.47 (m, 2H), 7.38 (d, 1H, J=7.6 Hz), 3.72 (m, 2H), 3.52 (d, 1H, J=5.4 Hz), 3.45 (m, 1H), 3.17 (m, 1H), 2.97 (ddd, 1H, J=12.6, 12.6, 2.6 Hz), 2.38–2.29 (m, 2H), 2.26 (s, 3H), 2.18–1.56 (m, 5H), 1.35 (dd, 6H, J=4.1, 2.6 Hz), 0.79 (t, 3H, J=7.3 Hz); $^{13}$C (CDCl$_3$)δ 209.8, 142.5, 135.1, 131.7, 131.5, 126.7, 125.1, 124.6, 124.4, 123.2, 121.7, 64.7, 62.8, 57.4, 42.2, 35.2, 34.9, 30.6, 28.4, 26.7, 25.2, 23.7, 23.3, 7.7; MS m/z (rel intensity) 349 (53), 292 (100), 264 (1), 250 (4), 193 (9), 178 (11), 165 (14), 153 (13); Anal. Cacld. for C$_{24}$H$_{31}$NO·0.9 H$_2$O: C, 78.82; H, 9.04; N, 3.83 Found C, 78.861; H, 8.77; N, 3.54.

3β-(2-(6-Ethylnaphthyl)-8-methyl-2β-(propanoyl)-8-azabicyclo [3.2.1]octane (WF-40). (98/2 ether/triethylamine-85/10/5 ether/triethylamine/methanol), 31% yield: IR (neat) 2959, 2936, 2875, 1718, 1692, 1514, 1459, 1449, 1130, 1109, 1054, 825 cm$^{-1}$; $^1$H NMR (CDCl$_3$) δ7.84–7.58 (m, 3H), 7.51 (s, 1H), 7.40 (m, 2H), 3.53 (d, 1H, J=4.1 Hz) 3.46 (m, 1H), 3.09 (m, 2H), 2.75 (q, 2H, J=7.7 Hz), 2.70 (m, 1H), 2.33–2.09 (m, 2H), 2.26 (s, 3H), 1.85–1.67 (m, 5H), 1.28 (t, 3H, J=7.6 Hz), 0.75 (t, 3H, J=7.3 Hz); $^{13}$C(CDCl$_3$)δ 210.6, 141.1, 139.5, 132.2, 131.8, 127.6, 127.1, 126.9, 125.8, 125.3, 125.1, 64.0, 62.5, 59.0, 41.9, 35.5, 34.2, 34.1, 28.9, 25.4, 25.1, 15.7, 7.6; MS m/z (rel intensity) 335 (47), 278 (100), 250 (6), 193 (11), 178 (23), 165 (34), 153 (26); Anal. Calcd. for C$_{23}$H$_{29}$NO: C, 82.33; E 8.72; N, 4.18 Found C, *; H, *; N, ***.

3β-(2-(6-isopropylnaphthyl))-8-methyl-2β-(propanoyl)-8-azabicyclo [3.2.1]octane (WF-41).

(98/2 ether/triethylamine-85/10/5 ether/triethylamine/methanol), 10.6 % yield: IR (neat) 2957, 2936, 2875, 2797, 1691, 1514, 1449, 1374, 1226, 973, 880 cm$^{-1}$; $^1$H NMR (CDCl$_3$)δ 7.69–7.52 (m, 4H), 7.31(dt, 2H, J=8.3, 2.4 Hz), 3.48 (d, 1H, J=5.6 Hz), 3.38 (m, 1H), 3.08 (m, 2H), 3.01 (m, 1H), 2.68 (ddd, 1H, J=11.8, 11.8, 2.4 Hz), 2.34–2.09 (m, 2H), 220 (s, 3H), 1.84–1.69 (m, 5H), 1.29 (d, 6H, J=7.0 Hz), 0.76 (t, 3H, J=7.3 Hz); $^{13}$C (CDCl$_3$)δ 210.2, 145.6, 139.9, 132.1, 132.0, 127.6, 127.1, 125.8, 125.6, 125.2, 123.0, 64.7, 62.4, 59.4, 42.1, 35.3, 34.4, 34.1, 26.5, 25.3, 23.9, 7.7; MS m/z (rel intensity) 349 (50), 292 (100), 264 (4), 250 (3), 193 (9), 178 (15), 165 (17), 153 (18); Anal. Calcd. for C$_{24}$H$_{31}$NO·0.5 H$_2$O; C, 80.39; H, 9.00; N, 3.91 Found C, 80.33; H, 8.73; N, 3.67.

3β-(2-(6-Methoxynaphthyl))-8-methyl-2α-(propanoyl)-8-azabicyclo [3.2.1]octane (WF-33). 199/1 ether/triethylamine), 59% yield, IR (neat) 2940, 1707, 1606, 1484, 1267, 851 cm$^{-1}$; $^1$H NMR (CDCl$_3$) δ 7.60–7.40 (m, 4H), 7.10 (m, 2H), 3.86 (s, 3H), 3.63 (dd, 1H, J=11.5, 2.1 Hz), 3.41 (d, 2H), 3.28 (ddd, 1H, J=11.5, 11.5, 5.6, Hz), 2.51 (s, 3H), 2.50 (dq, 1H, J=14.6, 7.3 Hz), 2.30 (dq, 1H, J=14.6, 7.3 Hz), 2.20–1.6(m, 6H), 16.71 (t, 3H, J=7.3 Hz); $^{13}$C (CDCl$_3$)δ 210.8, 157.3, 137.9, 133.4, 129.1, 128.8, 127.0, 126.6, 126.3, 118.6, 105.4, 63.5, 62.2, 57.2, 55.2, 39.8, 38.3, 36.9, 36.2, 26.0, 22.1, 7.2; MS m/z (rel intensity) 337 (87), 280 (100), 171 (9), 108 (4), 97 (55), 82 (91), 57 (10). Anal. Calcd for C$_{22}$H$_{27}$NO$_2$ 0.5H$_2$O: C, 76.27; H 8.15; N, 4.04 Found C, 76.37; H, 8.11; N, 4.05.

3β-(2-(5-Ethyl-6-methoxynaphthyl))-8-methyl-2β-propanoyl-8-azabicyclo [3.2.1]octane (WF-52). (99/1 ether/triethylamine), 19% yield: IR (neat): 1H NMR (CDCl$_3$) 7.85 (d, 1H, J=8.9 Hz), 7.63 (d, 1H, J=9.0 Hz), 7.58 (sbr, 1H), 7.37 (dd, 1H, J=8.9, 2.1 Hz), 7.21 (d, 1H, J=9.0 Hz), 3.92 (s, 3H), 3.51 (dbr, 1H, J=6.5 Hz), 3.43 (sbr, 1H), 3.16–2.96 (m, 4H), 2.71 (dd, 1H, J=12.4, 2.9 Hz), 2.42–2.04 (m, 3H), 2.24 (s, 3H), 1.87–1.56(m, 4H), 1.20 (t, 3H, J=7.5 Hz), 0.80 (t, 3H, J=7.3 Hz); $^{13}$C NMR (CDCl$_3$) 210.4, 153.5, 137.8, 131.1, 128.3, 127.1, 126.2, 125.5, 122.9, 114.0, 113.6, 64.7, 62.4, 59.3, 56.7, 42.1, 35.3, 34.4, 33.8, 26.5, 25.3, 18.2, 14.6, 7.7; MS mz/z (rel. intensity) 365 (25), 308 (51), 239 (2), 199 (5), 165 (8), 152 (8), 97 (59), 96 (57), 83 (97), 82 (100), 57 (32), 42 (48);

3β-(2-(5-isopropenyl-6-methoxynaphthyl))-8-methyl-2β-propanoyl-8-azabicyclo [3.2.1]octane (WF-65).

(50/50 ether/pertroleum ether, 2% triethylamine):

IR (neat) 3077, 2936, 1717, 1642, 1593, 1258, 1054 cm$^{-1}$; $^1$H NMR (CDCl$_3$) 7.82(d, 1H, J=8.9 Hz), 7.68 (d, 1H, J=9.0 Hz), 7.59 (sbr, 1H), 7.32 (dd, 1H, J=8.9, 1.7 Hz), 7.21 (d, 1H, J=9.0 Hz), 5.48 (sbr, 1H), 4.93 (sbr, 1H), 3.90 (s, 3H), 3.50 (dbr, 1H, J=6.3 Hz), 3.40 (dbr, 1H, J=5.3 Hz), 3.09 (m, 2H), 2.72 (tbr, 1H, J=12.5), 2.44–2.02 (m, 3H), 2.21 (s, 3H), 2.10 (s, 3H), 1.82–1.57 (m, 4H), 0.81 (t, 3H, J=7.3 Hz); $^{13}$C NMR (CDCl$_3$) 210.2, 152.2, 141.4, 138.2, 130.6, 129.0, 128.0, 126.8, 126.2, 125.4, 124.4, 116.3, 113.4, 64.6, 62.4, 59.2, 56.7, 42.0, 35.1, 34.3, 33.8, 26.4, 25.2, 24.0, 7.7; MS m/z (rel. intensity) 42 (40), 57 (26), 82 (93), 83 (100), 96 (62), 97 (70), 139 (3), 153 (8), 165 (11), 211 (7), 263 (2), 320 (47), 377 (30); Anal Calcd. for C$_{25}$H$_{31}$NO2·0.2H$_2$O: C, 78.79; H, 8.30; N, 3.63 Found C, 78.77; H, 8.66; N, 3.33.

2β-(propanoyl)-8-methyl-30-(2-(6-methoxy-5-nitronaphthyl))-8-azabicyclo [3.2.1]octane (WF-44):

To solution of WF-33 (20 mg, 0.059 mmol) in dry CH$_3$CN (10 ml) at 0° C. under Ar was added solid NO$_2$BF$_4$ (10.18 mg, 0.076 mmol) in one portion. The reaction mixture was stirred at 0°C. for 4 h, cooled to −10° C. and then ice (0.1 g) was added. The resulting solution was allowed to warm to room temperature and stirred overnight. The reaction mixture was filtered, and the filtrate was concentrated. The residue was made basic with NH$_4$OH solution (5 drops conc. NE4OH in 5 mL of water). The aqueous layer was saturated with NaCl and extracted with CH$_2$Cl$_2$ (3 ×20 mL). The organic layer was dreid (Na$_2$SO4) and removed under reduced pressure. Purification on alumina (neutral) column chromatography (95/5 ether/triethylamine) afforded WF-44: 11.9 mg (52.5% yield)IR(neat) 2938, 2851, 1713, 1636, 1608, 1527, 1507, 1355, 1281, 1262, 1218, 1079, 732 cm$^{-1}$; $^1$H NMR (CDCl$_3$)δ 7.88 (d, 1H, J=9.2 Hz), 7.6 (bs, 1H), 7.55 (d, 1H, J=8.8 Hz), 7.44 (dd, 1H, J=8.8, 1.6 Hz, 3.99 (s, 3H), 3.58 (d, 1H, J=7.1 Hz), 3.44 (m, 1H), 3.10 (m, 2H), 2.71 (ddd, 1H, J=12.9, 12.9, 2.6 Hz), 2.25 (s, 3H), 2.36 (dq, 1H, J=15.7, 7.3 Hz), 2.17 (dq, 1H, J=15.7, 7.3 Hz), 1.76 (m, 5H), 0.80 (t, 3H, J=7.3 Hz; $^{13}$C (CDCl$_3$)δ 209.6, 167.6, 148.1, 140.2, 132.1, 129.2, 128.3, 125.7, 124.0, 120.0, 112.9, 64.5, 62.4, 58.7, 57.1, 42.0, 35.0, 34.2, 34.0, 26.4, 25.3, 7.8; MS m/z (rel intensity) 382 (50), 325 (100), 297 (2), 178 (14), 153 (6), 108 (1), 97 (44), 82 (57), 57 (12).

3β-(2-(5-iodo-6-methoxynaphthyl))-8-methyl-2β-propanoyl-8-azabicyclo [3.2.1]octane (WF-48). To a solution of WF-33 (0.059 g, 0.175 mmol) and ICN (0.135 g, 0.88 mmol) in 20/80 ether/nitromethane (5 ml) was added a solution of aluminum chloride (0.117 g, 0.88 mmol) in nitromethane (5 ml). The mixture was stirred at room temperature for 48 h. The mixture was poured onto 10% aqueous Na?S$_2$O$_3$/CH$_2$Cl$_2$ and extracted with CH$_2$Cl$_2$. The organic layer was extracted with NaHCO$_3$, dried with MgSO₄, filtered, and the solvent was removed under reduced pressure. Prufication by silica gel column chromatography (50/50 ether/petroleum ether, 10% triethylamine) to afforded WF-48 as a white solid (0.049 g, 60% yield): IR (neat) 2940, 1714, 1597, 1252, 1064 cm⁻¹; ¹H NMR (CDCl₃) 7.97 (d, 1H, J=8.9 Hz), 7.75 (d, 1H, J=8.9 Hz), 7.57 (sbr, 1H), 7.41 (dd, 1H, J=8.9, 1.8 Hz), 7.17 (d, 1H, J=9.0 Hz), 4.00 (s, 3H), 3.55 (dbr, 1H, J=5.6 Hz), 3.45 (m, 1H), 3.12 (m, 2H), 2.71 (td, 1H, J=12.5, 2.8 Hz), 2.45–2.09 (m, 3H), 2.24 (s, 3H), 1.88–1.60 (m, 4H), 0.81 (t, 3H, J=7.3 Hz); ¹³C NMR (CDCl₃) 209.9, 156.2, 139.4, 134.1, 130.7, 130.2, 129.9, 128.1, 125.8, 112.9, 87.4, 64.6, 62.4, 59.1, 57.3, 42.1, 35.1, 34.3, 33.8, 26.4, 25.3, 7.8; MS m/z (rel. intensity) 463 (13), 406 (26), 280 (3), 152 (9), 97 (57), 96 (59), 83 (93), 82 (100), 55 (11, 44 (88). Anal. Calcd for $C_{22}H_{26}INO$: C, 57.03; H, 5.66; N, 3.02. Found C, 56.84; H, 5.71; N, 2.97.

3β-(5-acetyl-6-methoxynaphthyl)-8-methyl-2β-propanoyl-8-azabicyclo [3.2.1]octane (WF-53). To a stirred solution of acetyl chloride (0.0906 g, 1.15 mmol), and aluminum chloride (0.307 g, 2.3 mmol) in nitrobenzene (10 mL) was added over a period of 20 min a solution of WF-33 (0.326 g, 0.97 mmol) in nitrobenzene (20 mL). After stirring overnight at room temperature, the mixture was outed onto ice (100 g) and 10M HCl (30 mL) and then extracted with 3M HCl (3×). The aqueous layer was made basic with concentrated NH₄OH and extracted with CH₂Cl₂. The organic layer was dried (MgSO₄), filtered, and the solvent was removed under reduced pressure. Purification by silica gel column chromatography (50/50 petroleum ether/ether, 2% triethylamine) afforded WF-53 as a white solid (0.0233 g, 7.2% yield): IR (neat) 3155, 2941, 1715, 1685, 1598, 1255, 1012 cm⁻¹; ¹H NMR (CDCl₃) 7.79 (d, 1H, J=9.2 Hz), 7.63 (d, 1H, J=9.2 Hz), 7.60 (sbr, 1H), 7.32 (dd, 1H, J=8.8, 1.9 Hz), 7.21, (d, 1H, J=9.1 Hz), 3.93 (s, 3H), 3.51 (dbr, 1H, J=7.1 Hz), 3.42 (m, 1H), 3.08 (m, 2H), 2.72 (tbr, 1B, J=14.6 Hz), 2.60 (s, 3H), 2.42–2.05 (m, 3H), 2.23 (s, 3H), 1.86–1.61 (m, 4H), 0.79 (t, 3H, J=7.3 Hz); ¹³C NMR (CDCl₃) 210.1, 205.3, 153.7, 138.9, 131.5, 128.9, 128.7, 127.8, 125.8, 124.8, 123.3, 112.7, 64.5, 62.4, 58.9, 56.4, 42.0, 35.2, 34.1, 33.9, 32.7, 26.4, 25.2, 7.7; MS m/z (rel. intensity) 379 (17), 322 (44), 153 (3), 139 (3), 97 (56), 96 (55), 83 (90), 82 (100), 57 (27), 42 (52); Anal. Calcd for $C_{24}H_{29}NO_3 \cdot 0.4H_2O$; C, 74.93; H, 8.12; N, 3.64. Found C, 74.93; H, 7.90; N, 3.38.

2β-Propanoyl-3p-(4-methylphenyl)-8-azabicyclo [3.2.1]octane (WF-49). [5% triethylamine: 45% ether: 50% pentane) then [5% triethylamine: 95% ether], 46% yield; IR (CDCl₃) 3687, 3605, 2925, 1699, 1602, 1377, 1096 cm⁻¹; ¹H NMR (CDCl₃)δ: 7.03 (d, 2H, J=6.3 Hz), 7.02 (d, 2H, J=6.1 Hz), 3.71 (m, 1H), 3.58 (dbr, 1H, J=5.3 Hz), 3.18 (dt, 1H, J=13.1 and 5.3 Hz), 2.88 (d br, 1H, J=5.3 Hz), 2.81 (s, br, 1H), 2.40 (td, 1H, J=13.1 and 2.8 Hz), 2.21–2.00 (m, 3H), 1.79–1.50 (m, 4H), 0.67 (t, 3H, J=7.2 Hz); ¹³C NMR (CDCl₃)δ: 215.3, 139.0, 136.1, 129.1, 127.4, 56.2, 55.8, 53.6, 38.8, 36.2, 33.8, 29.0, 27.5, 21.0, 7.0; MS m/z 257 (M+, 29%), 239 (30), 237 (21), 210 (32), 208 (32), 200 (39), 159 (7), 148 (10), 142 (10), 128 (15), 118 (26), 117 (26), 115 (27), 105 (20), 91 (30), 83 (86), 82 (60), 69 (76), 68 (100), 57 (36), 54 (20), 41 (32). Anal. Calcd for $C_{19}H_{27}NO \cdot 0.25H_2O$: C, 78.71; H, 9.56; N, 4.83. Found:C, 78.73; H, 9.58; N, 4.72.

2β-Propanoyl-3β-(4-(1-methylethyl)phenyl)-8-azabicyclo [3.2.1]octane (WF-51). [5% triethylamine: 45% ether: 50% pentane], 48% yield; IR (CDCl₃) 3691, 3607, 2963, 1695, 1602, 1460, 1406, 1377, 1097 cm⁻¹; ¹H NMR (CDCl₃)δ: 7.09 (d, 2H, J=8.4 Hz), 7.05 (d, 2H, J=8.4 Hz), 3.69 (m, 1H), 3.55 (d br 1H, J=5.2 Hz), 3.19 (ddd, 1H, J=12.7, 5.4 and 5.4 Hz), 2.87 (d br, 1H, J=5.8 Hz), 2.83 (septet, 1H, J=7.0 Hz), ca. 2.45 (s br, 1H), 2.40 (ddd, 1H, J=13.1, 13.1 and 2.9 Hz), 2.17 (q, 1H, J=7.3 Hz), 2.08 (q, 1H, J=7.3 Hz), 2.05 (m, 1H), 1.77–1.48 (m, 4H), 1.18 (d, 6H, J=7.0 Hz), 0.64 (t, 3H, J=7.2 Hz); ¹³C NMR (CDCl₃)δ: 215.3, 147.1, 139.5, 127.4, 126.3, 56.3, 55.8, 53.5, 38.7, 36.1, 33.8, 33.6, 29.1, 27.6, 24.0, 23.9, 6.9; MS m/z 285 (26%, M+), 238 (3), 228 (35), 187 (5), 131 (11), 128 (12), 115 (12), 83 (100), 68 (74), 57 (24), 41 (24). Anal. Calcd for $C_{19}H_{27}NO \cdot 0.25H_2O$: C, 78.71; H, 9.56; N, 4.83. Found C, 78.73; H, 9.58; N, 4.72:

2β-Propanoyl-3β-(2-naphthyl)-8-azabicyclo [3.2.1] octane (WF-50). [5% triethylamine: 95% ether], 49% yield; IR (CDCl₃)3692, 3607, 2940, 1695, 1602, 1470 cm⁻¹; ¹H NMR (CDCl₃)δ: 7.75 (m, 3H), 7.56 (s, br 1H), 7.42 (m, 2H), 7.30 (dd, 1H, J=8.5 and 1.8 Hz), 3.75 (ddd, 1H, J=6.3, 3.1 and 3.1 Hz), 3.60 (d, br, 1H, J=5.7 Hz), 3.37 (ddd, 1H, J=12.7, 5.4 and 5.4 Hz), 3.01 (d, br, 1H, J=5.9 Hz), 2.57 (ddd, 1H, J=13.0, 13.0 and 2.9 Hz), ca. 2.50–2.45 (s, br, 1H), 2.19 (q, 1H, J=7.2 Hz), 2.1Q (q, 1H, J=7.2 Hz), 2.09 (m, 1H), 1.84–1.50 (m, 4H), 1.18 (d, 6H, J=7.0 Hz), 0.59 (t, 3H, J=7.2 Hz); ¹³C NMR (CDCl₃)δ: 214.9, 139.9, 133.4, 132.2, 127.9, 127.8, 127.5, 126.2, 126.0, 125.5, 56.3, 55.9, 53.6, 38.7, 36.8, 34.0, 29.2, 27.7, 24.0, 7.0; MS m/z 293 (M+, 43%), Z75 (11), 244 (9), 236 (49), 222 (9), 195 (6), 178 (19), 165 (23), 152 (27), 141 (15), 128 (16), 83 (100), 82 (80), 68 (97), 57 (29), 41 (22). Anal. Calcd for $C_{20}H_{23}NO \cdot 0.7H_2O$: C, 78.50; H, 8.04; N, 4.58. Found: C, 78.46; H, 7.69; N, 4.58.

3β-(4-(1-ethylpropyl)phenyl)-8-methyl-2β-propanoyl-8-azabicyclo [3.2.1]octane (WF-61). [pentane-(49% ether: 49% pentane: 2% triethylamine)], 27% yield; IR (neat) 2957, 2931, 1713, 1457, 1362 cm⁻¹; ¹H NMR (CDCl₃)δ 7.13 (d, 2H, J=8.2 Hz), 7.01 (d, 2H, J=8.2 Hz), 3.43 (dbr, 1H, J-6.9 Hz), 3.37 (m, 1H), 2.98 (m, 2H), 2.59 (td, 1H, J=12.3, 2.8 Hz), 2.31–2.06 (m, 4H), 2.20 (s, 3H), 1.80–1.41 (m, 8H), 0.79 (t, 3H, J=6.9 Hz), 0.72 (t, 6H, J=7.3 Hz); ¹³C NMR (CDCl₃)δ 210.8, 143.1, 140.3, 127.5, (2 CH), 127.0, (2 CH), 64.6, 62.4, 59.5, 49.2, 42.0, 35.6, 34.3, 33.6, 29.2, 29.1, 26.5, 25.2, 12.2, 7.7; MS m/z (rel. intensity) 42 (38), 57 (28), 82 (90), 83 (100), 96 (54), 97 (70), 107 (13), 115 (8), 128 (8), 153 (6), 226 (3), 242 (4), 270 (48), 327 (26). Anal. Calcd for $C_{22}H_{33}NO$: C, 80.68; H, 10.16; N, 4.28. Found C, 80.90; H, 10.18; N, 4.07.

3β-(4-(1-ethylpropyl)phenyl)-2β-propanoyl-8-azabicyclo (3.2.1]octane (WF-62). [(49% ether: 49% pentane: 2% triethylamine)-(98% ether: 2% triethylamine)], 46% yield; IR (neat) 3309, 2961, 2931, 1698, 1460, 1375 cm⁻¹; ¹H NMR (CDCl₃)δ 7.06 (d, 2H, J=7.7 Hz), 7.02 (d, 2H, J=8.8 Hz), 3.71 (sbr, 1H), 3.56 (dbr, 1H, J=6.0 Hz), 3.24 (dt, 1H, J=12.7, 5.6 Hz), 2.85 (dbr, 1H, J=5.8 Hz), 2.85 (sbr, 1H), 2.42 (td, 1H, J=13.1, 2.8 Hz), 2.30–2.15 (m, 1H), 2.13–1.96 (m, 3H), 1.78–1.40 (m, 8H), 0.70 (t, 6H, J=7.3 Hz), 0.61 (t, 3H, J=7.2 Hz); ¹³C NMR (CDCl₃)δ 215.4, 143.9, 139.5, 127.8 (2 CH), 127.3 (2CH), 55.7, 53.4, 49.2, 38.9, 36.3, 33.6, 29.3, 29.2, 29.1, 27.5, 12.0, 6.8; MS m/z (rel. intensity) 313 (17), 295 (10), 266 (16), 256 (31), 215 (11), 175 (3), 148 (6), 128 (9), 117 (14), 83 (50), 82 (31), 69 (100), 57 (33), 41 (22). Anal. Calcd. for $C_{21}H_{31}NO \cdot 0.3H_2O$: C, 79.1; H, 9.99; N, 4.39. Found C, 78.98; H, 9.85; N, 4.29.

3β-(4-cyclohexylphenyl)-8-methyl-2β-propanoyl-8-azabicyclo [3.2.1]octane (WF-63). [pentane-(49% ether: 49% pentane: 2% triethylamine)], 27% yield; IR (neat) 2925, 2850, 1718, 1690 cm⁻¹; ¹H NMR (CDCl₃)δ 7.14 (d, 2H, J=8.4 Hz), 7.07 (d, 2 H, J=8.4 Hz), 3.46 (dbr, 1H, J=6.3 Hz), 3.36 (sbr, 1H), 2.98 (m, 2H), 2.58 (td, 1H, J=12.2, 2.9 Hz), 2.46–2.05 (m, 4H), 2.20 (s, 3H), 1.84–1.52 (m, 9H), 1.47–1.17 (m, 5H), 0.84 (t, 3H, J=7.3 Hz); ¹³C NMR (CDCl₃)δ 210.4, 145.2, 140.4, 126.9 (2CH), 126.4 (2CH) 64.5, 62.4, 59.3, 44.0, 42.0, 35.2, 34.4, 34.2, 33.6, 26.9, 26.4, 26.1, 25.2, 7.7; MS m/z (rel. intensity) 339, (25), 282 (51), 241 (3), 200 (2), 173 (3), 153 (8), 115 (10), 97 (76), 96 (62), 83 (100), 82 (90), 55 (35), 42 (43). Anal. Calcd. for $C_{23}H_{33}NO$: C, 81.37; H, 9.8; N, 4.13. Found C, 81.25; H, 9.83; N, 4.02.

The general activity of this group of novel tropane derivatives demonstrates that they have potential for the treatment of diseases associated with monoamine imbalances such as depression, attention-deficit hyperactivity disorder, obesity, and obsessive-compulsive disorders as well as aiding in the treatment of cocaine addiction.

at the 5 position and further providing that when Ar is 1-naphthyl or 2-naphthyl that $R_1$ is hydrogen;

$R_1$ is hydrogen or $C_1$ to $C_8$ alkyl;

$R_2$ and $R_3$ are the same or different and are selected from the group consisting of hydrogen and $C_1$ to $C_8$ ketones, with only one of $R_2$ and $R_3$ being hydrogen at any one time;

wherein the 3-aryltropane is administered in a dosage of from 4 micrograms/Kg to 50 milligrams/Kg.

2. The method of claim 1 wherein the mammal is the human species.

3. The method of claim 2 wherein the administration is by a method selected from the group consisting of oral, intravenous, and parenteral.

TABLE 1

$IC_{50}$ and K1 values of tropane analogs in displaying [125]RTI binding. [3H]paroxetine binding and [3H]nisoxetine binding in rat brain membranes

| Analog | $R_1$ | Ar | [³H]paroxetine (5-HT) K1(nM) | [125]RTI-55 (DA) $IC_{50}$(nM) | [3H]nisoxetine (NE) K1(nM) | 5HT/DA Potency Ratio | 5-HT/NE Potency Ratio | DA/NE Potency Ra |
|---|---|---|---|---|---|---|---|---|
| (WF 11) | CH₃ | 4-methylphenyl | 130 ± 10 | 8.2 ± 1.6 | 160 ± 1.6 | 0.063 | 1.2 | 20 |
| (WF 23) | CH₃ | 2-naphthyl | 0.39 ± 0.07 | 0.12 ± 0.02 | 2.9 ± 0.50 | 0.31 | 7.4 | 24 |
| (WF 31) | CH₃ | 4-isoproplphenyl | 36 ± 4.4 | 440 ± 41 | >10,000 | 12 | >280 | >23 |
| (WF 30) | CH₃ | 1-naphthyl | 21 ± 1.9 | 5.3 ± 1.3 | 39 ± 9.9 | 0.25 | 1.9 | 7.4 |
| (WF 27) | CH₃ | 4-methyl-1-naphthyl | 9.0 ± 1.7 | 25 ± 0.5 | ND | 2.8 | ND | ND |
| (WF 42) | CH₃ | 4-ethyl-1-naphthyl | 140 ± 40.5 | 88 ± 14 | 4800 ± 690 | 0.62 | 34 | 55 |
| (WF 38) | CH₃ | 4-isopropyl-1-naphthyl | 140 ± 64 | 230 ± 36 | >10,000 | 1.6 | >71 | >43 |
| (WF 40) | CH₃ | 6-ethyl-2-naphthyl | 1.1 ± 0.76 | 0.34 ± 0.10 | 28 ± 9.6 | 0.30 | 25 | 82 |
| (WF 41) | CH₃ | 6-isopropyl-2-naphthyl | 2.0 ± 0.33 | 0.59 ± 0.21 | 30 ± 5.2 | 0.30 | 15 | 51 |
| (WF 33) | CH₃ | 6-methoxy-2-naphthyl | 1.1 ± 0.76 | 0.43 ± 0.19 | ND | 0.39 | ND | ND |
| (WF 44) | CH₃ | 6-methoxy-5-nitro-2-naphthyl | 15 ± 1.6 | 150 ± 50 | 890 ± 140 | 10 | 59 | 6.0 |
| (WF 48) | CH₃ | 5-iodo-methoxy-2-naphthyl | 2.2 ± 0.31 | 1.3 ± 0.33 | 78 ± 80 | 0.6 | 355 | 600 |
| (WF 65) | CH₃ | 6-methoxy-5-(methylethenyl)-2-napththyl | 88 ± 13.3 | 45 ± 3.7 | 2700 ± 280 | 0.5 | 31 | 60 |
| (WF 52) | CH₃ | 5-ethyl-6-methoxy-2-naphthyl | 7.2 ± 1.8 | 33 ± 8.9 | 340 ± 50 | 4.6 | 470 | 100 |
| (WF 53) | CH₃ | 5-acetyl-6-methoxy-2-naphthyl | 16 ± 2.1 | 13 ± 3.4 | 500 ± 24 | 0.81 | 31 | 38 |
| (WF 49) | H | 4-methylphenyl | 19 ± 1.4 | 4.7 ± .58 | 5.5 ± 2.0 | 0.25 | 0.29 | 1.2 |
| (WF 51) | H | 2-naphthyl | 0.16 ± 0.13 | 0.050 ± 0.01 | 2.0 ± 0.09 | 0.31 | 12 | 40 |
| (WF 50) | H | 4-isopropylphenyl | 5.3 ± 1.0 | 380 ± 110 | 3400 ± 270 | 72 | 640 | 8.9 |
| (WF 61) | CH₃ | 4-(3-pentyl)phenyl | 540 ± 51 | 270 ± 38 | >10,000 | 0.5 | >19 | >37 |
| (WF 62) | H | 4-(3-pentyl)phenyl | 150 ± 50 | 190 ± 17 | 5100 ± 220 | 1.27 | 34 | 27 |
| (WF 63) | CH₃ | 4-cyclohexylphenyl | 97 ± 12 | 320 ± 55 | >10000 | 3.3 | >100 | >31 |
| (WF 64) | H | 4-cyclohexylphenyl | 85 ± 16 | 490 ± 120 | 4300 ± 1100 | 5.8 | 51 | 8.8 |
| (WF 55) | CH₃ | 4-(ethenyl)phenyl | 3.2 ± 1.3 | 0.90 ± 0.34 | 78 ± 31 | 0.28 | 24 | 87 |
| (WF 58) | H | 4-(ethenyl)phenyl | 0.32 ± 0.06 | 1.5 ± 1.1 | 10.9 ± 1.5 | 4.7 | 34 | 7.3 |
| (WF 54) | CH₃ | 4-(1-methylethenyl)phenyl | 0.82 ± 0.38 | 7.2 ± 2.1 | 794 ± 10 | 8.8 | 970 | 10 |
| (WF 60) | H | 4-(1-methylethenyl)phenyl | 0.10 ± 0.02 | 16 ± 5 | 94 ± 18 | 160 | 940 | 5.9 |

What is claimed is:

1. A method of treating mammals to selectively block serotonin uptake comprising:
administering a 3-aryltropane derivative of the formula:

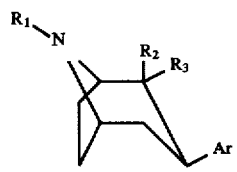

and structural isomers thereof, wherein

Ar is an aromatic moiety selected from the group consisting of 1-naphthyl, 2-naphthyl, 4-(substituted $C_1$ to $C_8$ alkyl)-1-naphthyl, 6-(substituted $C_1$ to $C_8$ alkyl)-2-naphthyl, 6-methoxy-5-substituted-2-naphthyl (where the 5-substituent is $C_1$ to $C_8$ alkyl, iodo, nitro or acyl), phenyl, 4-(substituted $C_1$ to $C_8$ alkyl)phenyl, 4-substituted vinylphenyl, and 4-(substituted $C_1$ to $C_8$ -alkyl)phenyl moiety, and further providing that when $R_1$ is methyl and Ar is a naphthyl that Ar is substituted 4. The method of claim 1 wherein the dosage is oral at a level of from 20 micrograms/Kg to 15 mg/Kg.

5. The method of claim 1 wherein $R_1$ is hydrogen.

6. The method of claim 5 wherein Ar is 4-(1-methylethenyl) phenyl.

7. A 3-aryltropane derivative having the following formula:

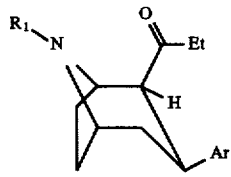

and structural isomers thereof, wherein

Ar is an aromatic moiety selected from the group consisting of 1-naphthyl, 2-naphthyl, 4-(substituted $C_1$ to $C_8$ alkyl)-1-naphthyl, 6-(substituted $C_1$ to $C_8$ alkyl)-2-naphthyl, 6-methoxy-5-substituted-2-naphthyl (where the 5-substituent is $C_1$ to $C_8$ alkyl, iodo, nitro or acyl), phenyl, 4-(substituted $C_1$ to $C_8$ alkyl)phenyl, 4-substituted vinylphenyl, and 4-(substituted $C_1$ to $C_8$ 1-alkyl)phenyl moiety, and further providing that when $R_1$ is methyl and Ar is a naphthyl that Ar is substituted at the 5 position and further providing that when Ar is 1-naphthyl or 2-naphthyl that $R_1$ is hydrogen; and $R_1$ is hydrogen or $C_1$ to $C_8$ alkyl.

8. A 3-aryltropane according to claim 7 wherein Ar is vinylphenyl.

9. A 3-aryltropane according to claim 7 wherein Ar is 4-(substituted C1 to C8 1-alkenyl)phenyl moiety.

10. A 3-aryltropane according to claim 7 wherein $R_1$ is hydrogen.

11. A 3-aryltropane according to claim 10 wherein Ar is 4-(1-methylethenyl)phenyl.

* * * * *